United States Patent
Rodrigues et al.

(10) Patent No.: US 11,253,438 B2
(45) Date of Patent: *Feb. 22, 2022

(54) AEROSOL DEVICE FOR DRY-WASHING AND TREATING THE HAIR

(71) Applicant: L'OREAL, Paris (FR)

(72) Inventors: Céférino Rodrigues, Saint-Ouen (FR); Lionel Aubert, Saint-Ouen (FR); Catherine Tetu, Saint-Ouen (FR)

(73) Assignee: L'OREAL, Paris (FR)

(*) Notice: Subject to any disclaimer, the term of this patent is extended or adjusted under 35 U.S.C. 154(b) by 0 days.

This patent is subject to a terminal disclaimer.

(21) Appl. No.: 16/491,372

(22) PCT Filed: Mar. 9, 2018

(86) PCT No.: PCT/EP2018/055882
§ 371 (c)(1),
(2) Date: Sep. 5, 2019

(87) PCT Pub. No.: WO2018/162701
PCT Pub. Date: Sep. 13, 2018

(65) Prior Publication Data
US 2020/0016044 A1    Jan. 16, 2020

(30) Foreign Application Priority Data
Mar. 9, 2017  (FR) ..................... 1751944

(51) Int. Cl.
*A61K 8/02* (2006.01)
*A61K 8/04* (2006.01)
(Continued)

(52) U.S. Cl.
CPC ............ *A61K 8/0241* (2013.01); *A61K 8/046* (2013.01); *B05B 1/14* (2013.01); *B65D 83/28* (2013.01);
(Continued)

(58) Field of Classification Search
CPC ........ A61K 8/0241; A61K 8/046; A61K 8/19; A61K 2800/31; A61K 2800/412;
(Continued)

(56) References Cited

U.S. PATENT DOCUMENTS 2,047,398 A    7/1936  Voss et al.
2,102,113 A    12/1937  Djordjevitch
(Continued)

FOREIGN PATENT DOCUMENTS

DE    2330956 A1    1/1974
DE    102005025016 A1    12/2005
(Continued)

OTHER PUBLICATIONS

NPL search string attached; IQQueryQuickExport 202005221756; downloaded May 22, 2020.*

(Continued)

*Primary Examiner* — Jeffrey T. Palenik
(74) *Attorney, Agent, or Firm* — The Marbury Law Group, PLLC (57) ABSTRACT

The present invention relates to an aerosol device comprising:
  a container containing a cosmetic composition which comprises at least 6% by weight of one or more powders relative to the total weight of the composition, and
  a dispensing head comprising a body and an end part comprising at least two outlet orifices configured to allow spraying of the composition about a longitudinal axis of the end part in at least two different directions, the dispensing head comprising at least first and second chambers, through which the composition stream successively passes before it exits via the outlet orifices.

20 Claims, 7 Drawing Sheets

(51) Int. Cl.
  *B05B 1/14* (2006.01)
  *B65D 83/28* (2006.01)
  *B65D 83/14* (2006.01)
  *A61K 8/19* (2006.01)
  *A61K 8/46* (2006.01)
  *A61K 8/73* (2006.01)
  *A61K 8/81* (2006.01)
  *A61K 8/85* (2006.01)
  *A61K 8/88* (2006.01)
  *A61Q 5/02* (2006.01)
  *A61K 8/25* (2006.01)
  *A61K 8/26* (2006.01)

(52) U.S. Cl.
  CPC .............. *B65D 83/752* (2013.01); *A61K 8/19* (2013.01); *A61K 8/463* (2013.01); *A61K 8/732* (2013.01); *A61K 8/8147* (2013.01); *A61K 8/85* (2013.01); *A61K 8/88* (2013.01); *A61K 2800/31* (2013.01); *A61K 2800/412* (2013.01); *A61K 2800/87* (2013.01)

(58) Field of Classification Search
  CPC ........ A61K 2800/87; A61K 8/25; A61K 8/26; A61K 8/463; A61K 8/732; A61K 8/8147; A61K 8/85; A61K 8/88; B05B 1/14; B65D 83/28; B65D 83/752; A61Q 5/02
  See application file for complete search history.

(56) References Cited

U.S. PATENT DOCUMENTS

| | | | |
|---|---|---|---|
| 2,723,248 A | 11/1955 | Wright | |
| 3,161,460 A | 12/1964 | Huber | |
| 3,504,862 A | 4/1970 | Lowry | |
| 3,579,629 A | 5/1971 | Pasero et al. | |
| 3,589,978 A | 6/1971 | Kamal et al. | |
| 3,628,733 A | 12/1971 | Kahn | |
| 3,716,633 A | 2/1973 | Viout et al. | |
| 3,767,125 A | 10/1973 | Gehres et al. | |
| 3,792,068 A | 2/1974 | Luedders et al. | |
| 3,810,977 A | 5/1974 | Levine et al. | |
| 3,836,537 A | 9/1974 | Boerwinkle et al. | |
| 3,910,862 A | 10/1975 | Barabas et al. | |
| 3,925,542 A | 12/1975 | Viout et al. | |
| 3,946,749 A | 3/1976 | Papantoniou | |
| 3,966,403 A | 6/1976 | Papantoniou et al. | |
| 3,966,404 A | 6/1976 | Papantoniou et al. | |
| 3,990,459 A | 11/1976 | Papantoniou | |
| 4,031,307 A | 6/1977 | DeMartino et al. | |
| 4,128,631 A | 12/1978 | Landmark et al. | |
| 4,129,711 A | 12/1978 | Viout et al. | |
| 4,131,576 A | 12/1978 | Iovine et al. | |
| 4,137,208 A | 1/1979 | Elliott | |
| 4,165,367 A | 8/1979 | Chakrabarti | |
| 4,223,009 A | 9/1980 | Chakrabarti | |
| 4,282,203 A | 8/1981 | Jacquet et al. | |
| 4,289,752 A | 9/1981 | Mahieu et al. | |
| 4,401,271 A | 8/1983 | Hansen | |
| 4,450,151 A | 5/1984 | Shinozawa | |
| 4,557,916 A | 12/1985 | Witham | |
| 4,605,553 A | 8/1986 | Passalacqua | |
| 4,693,925 A | 9/1987 | Cheung et al. | |
| 4,728,571 A | 3/1988 | Clemens et al. | |
| 4,822,596 A | 4/1989 | Callingham et al. | |
| 4,871,529 A | 10/1989 | Sramek | |
| 4,874,554 A | 10/1989 | Lange et al. | |
| 4,957,732 A | 9/1990 | Grollier et al. | |
| 4,972,037 A | 11/1990 | Garbe et al. | |
| 4,983,377 A | 1/1991 | Murphy et al. | |
| 5,297,739 A | 3/1994 | Allen | |
| 5,300,284 A | 4/1994 | Wiechers et al. | |
| 5,508,259 A | 4/1996 | Holzner et al. | |
| 5,538,717 A | 7/1996 | La Poterie | |
| 5,614,173 A | 3/1997 | Ulmer et al. | |
| 5,643,557 A | 7/1997 | Eteve et al. | |
| 5,690,924 A | 11/1997 | Keil et al. | |
| 5,879,669 A | 3/1999 | Clausen et al. | |
| 5,900,241 A | 5/1999 | Roulier et al. | |
| 6,106,813 A | 8/2000 | Mondet et al. | |
| 6,166,093 A | 12/2000 | Mougin et al. | |
| 6,210,689 B1 | 4/2001 | Martino et al. | |
| 6,245,324 B1 | 6/2001 | Hough et al. | |
| 6,319,959 B1 | 11/2001 | Mougin et al. | |
| 6,350,434 B1 | 2/2002 | Bhatt et al. | |
| 6,372,876 B1 | 4/2002 | Kim et al. | |
| 6,395,265 B1 | 5/2002 | Mougin et al. | |
| 6,415,992 B1 | 7/2002 | Blondeel et al. | |
| 6,589,509 B2 | 7/2003 | Keller et al. | |
| 6,592,854 B1 | 7/2003 | Dupuis | |
| 6,751,886 B2 | 6/2004 | Chang et al. | |
| 7,063,834 B2 | 6/2006 | Mougin et al. | |
| 7,585,824 B2 | 9/2009 | Popplewell et al. | |
| 10,440,140 B2 | 10/2019 | Barraclough et al. | |
| 10,532,880 B2 | 1/2020 | Smail et al. | |
| 2002/0017575 A1 | 2/2002 | Andrews et al. | |
| 2002/0031478 A1 | 3/2002 | Keller et al. | |
| 2002/0150546 A1 | 10/2002 | Mougin et al. | |
| 2003/0150624 A1 | 8/2003 | Rummel | |
| 2003/0150937 A1 | 8/2003 | Laidler et al. | |
| 2003/0163878 A1 | 9/2003 | Pruche | |
| 2003/0185777 A1 | 10/2003 | Banowski et al. | |
| 2003/0191271 A1 | 10/2003 | Mondet et al. | |
| 2004/0047812 A1 | 3/2004 | Pataut et al. | |
| 2004/0170575 A1 | 9/2004 | Belli et al. | |
| 2004/0175404 A1 | 9/2004 | Shefer et al. | |
| 2005/0163737 A1 | 7/2005 | Lemoine et al. | |
| 2005/0220723 A1 | 10/2005 | Benabdillah et al. | |
| 2005/0224524 A1 | 10/2005 | Khan et al. | |
| 2008/0019928 A1 | 1/2008 | Franzke et al. | |
| 2008/0172807 A1 | 7/2008 | Brun | |
| 2008/0274071 A1 | 11/2008 | Kaplan et al. | |
| 2009/0061004 A1 | 3/2009 | Birkel et al. | |
| 2009/0218418 A1 | 9/2009 | Sharief | |
| 2010/0040572 A1 | 2/2010 | Mougin | |
| 2012/0097180 A1 | 4/2012 | Harris et al. | |
| 2012/0171264 A1 | 7/2012 | Bernet et al. | |
| 2012/0258052 A1 | 10/2012 | Mueller et al. | |
| 2012/0282190 A1 | 11/2012 | Hammer | |
| 2013/0289080 A1 | 10/2013 | Masse et al. | |
| 2013/0340786 A1 | 12/2013 | Rodrigues et al. | |
| 2014/0030196 A1 | 1/2014 | Russell et al. | |
| 2014/0079747 A1 | 3/2014 | Dihora et al. | |
| 2015/0014443 A1 | 1/2015 | Albisetti | |
| 2015/0041559 A1 | 2/2015 | Albisetti | |
| 2015/0104397 A1 | 4/2015 | Smail et al. | |
| 2015/0139917 A1 | 5/2015 | Gawtrey et al. | |
| 2016/0075501 A1 | 3/2016 | Aubert et al. | |
| 2016/0100667 A1 | 4/2016 | Aubert et al. | |
| 2016/0106634 A1 | 4/2016 | Gawtrey et al. | |
| 2018/0000700 A1 | 1/2018 | Smail et al. | |
| 2018/0016087 A1 | 1/2018 | Smail et al. | |
| 2018/0243763 A1 | 8/2018 | Eurippini | |

FOREIGN PATENT DOCUMENTS

| | | |
|---|---|---|
| DE | 102008035013 A1 | 1/2010 |
| EP | 0080976 A1 | 6/1983 |
| EP | 0095238 A2 | 11/1983 |
| EP | 0186507 A2 | 7/1986 |
| EP | 0342834 A2 | 11/1989 |
| EP | 0412704 A2 | 2/1991 |
| EP | 0412707 A1 | 2/1991 |
| EP | 0452208 A1 | 10/1991 |
| EP | 0530974 A1 | 3/1993 |
| EP | 0582152 A2 | 2/1994 |
| EP | 0619111 A1 | 10/1994 |
| EP | 0637600 A1 | 2/1995 |
| EP | 0648485 A1 | 4/1995 |
| EP | 0751162 A1 | 1/1997 |
| EP | 0974332 A1 | 1/2000 |
| EP | 1026220 A1 | 8/2000 |
| EP | 1407754 A1 | 4/2004 |

(56) References Cited

FOREIGN PATENT DOCUMENTS

| | | | |
|---|---|---|---|
| EP | 2444160 A1 | 4/2012 |
| EP | 2777770 A1 | 9/2014 |
| FR | 1222944 A | 6/1960 |
| FR | 1400366 A | 5/1965 |
| FR | 1564110 A | 4/1969 |
| FR | 1578989 A | 8/1969 |
| FR | 1580545 A | 9/1969 |
| FR | 1600138 A | 7/1970 |
| FR | 2077143 A5 | 10/1971 |
| FR | 2198719 A1 | 4/1974 |
| FR | 2265781 A1 | 10/1975 |
| FR | 2265782 A1 | 10/1975 |
| FR | 2350384 A1 | 12/1977 |
| FR | 2357241 A2 | 2/1978 |
| FR | 2393573 A1 | 1/1979 |
| FR | 2434194 A1 | 3/1980 |
| FR | 2439798 A1 | 5/1980 |
| FR | 2589476 A1 | 5/1987 |
| FR | 2715841 A1 | 8/1995 |
| FR | 2743297 A1 | 7/1997 |
| FR | 2814943 A1 | 4/2002 |
| FR | 2924341 A1 | 6/2009 |
| FR | 2980125 A1 | 3/2013 |
| FR | 2985201 A1 | 7/2013 |
| FR | 2985202 A1 | 7/2013 |
| FR | 2990131 A1 | 11/2013 |
| FR | 2990133 A1 | 11/2013 |
| FR | 3004901 A1 | 10/2014 |
| FR | 3004902 A1 | 10/2014 |
| FR | 3004929 A1 | 10/2014 |
| FR | 3031437 A1 | 7/2016 |
| GB | 839805 A | 6/1960 |
| GB | 922457 A | 4/1963 |
| GB | 1021400 A | 3/1966 |
| GB | 1218222 A | 1/1971 |
| GB | 1235894 A | 6/1971 |
| GB | 1331819 A | 9/1973 |
| GB | 1408388 A | 10/1975 |
| GB | 1572626 A | 7/1980 |
| GB | 2340891 A | 3/2000 |
| JP | 2003-326197 A | 11/2003 |
| JP | 2011-213619 A | 10/2011 |
| LU | 75370 A1 | 2/1978 |
| LU | 75371 A1 | 2/1978 |
| WO | 93/23009 A1 | 11/1993 |
| WO | 94/03510 A1 | 2/1994 |
| WO | 95/00578 A1 | 1/1995 |
| WO | 98/43599 A1 | 10/1998 |
| WO | 02/078653 A1 | 10/2002 |
| WO | 02/096379 A1 | 12/2002 |
| WO | 03/045573 A1 | 6/2003 |
| WO | 03/049711 A2 | 6/2003 |
| WO | 2004/043608 A1 | 5/2004 |
| WO | 2011/019539 A2 | 2/2011 |
| WO | 2011/056625 A1 | 5/2011 |
| WO | 2012/035053 A1 | 3/2012 |
| WO | 2012/080255 A2 | 6/2012 |
| WO | 2013/064918 A1 | 5/2013 |
| WO | 2013/167530 A2 | 11/2013 |
| WO | 2013/167536 A2 | 11/2013 |
| WO | 2014/177646 A2 | 11/2014 |
| WO | 2014/177647 A1 | 11/2014 |
| WO | 2014/177649 A1 | 11/2014 |
| WO | 2016/001190 A1 | 1/2016 |
| WO | 2016/005703 A1 | 1/2016 |
| WO | 2016/066729 A1 | 5/2016 |
| WO | 2016/066730 A1 | 5/2016 |
| WO | 2016/092109 A1 | 6/2016 |
| WO | 2016/110575 A1 | 7/2016 |
| WO | 2016/110578 A1 | 7/2016 |
| WO | 2016/110579 A1 | 7/2016 |
| WO | 2018/162707 A1 | 9/2018 |
| WO | 2018/162711 A1 | 9/2018 |

OTHER PUBLICATIONS

NPL search string attached; IQQueryQuickExport 202005221759; downloaded May 22, 2020.*
International Search Report and Written Opinion for counterpart Application No. PCT/EP2018/055882, dated May 4, 2018.
International Search Report and Written Opinion for counterpart Application No. PCT/EP2018/055889, dated May 4, 2018.
International Search Report and Written Opinion for counterpart Application No. PCT/EP2018/055904, dated Apr. 30, 2018.
Brunauer et al., "Adsorption of Gases in Multimolecular Layers," Journal of the American Chemical Society, vol. 60, Feb. 1938, pp. 309-319.
International Search Report for counterpart Application No. PCT/EP2013/059382, dated Jun. 20, 2014.
International Search Report for counterpart Application No. PCT/EP2013/059393, dated Jun. 20, 2014.
Database WPI Week 201172, Thomas Scientific, London, GB, AN 2011-N36295, XP002690571 (Jan. 25, 2013).
Mintel: Apr. 2010, "Refresh Dry Shampoo".
Mintel: Jun. 2011, "Brown Hair Powder Shampoo".
Oscar Blandi, http://www.skinstore.com/p-6885-oscar-blandi-pronto-dry-shampoo-spray.aspx. Published Jun. 13, 2011.
Non-Final Office Action for U.S. Appl. No. 14/399,753, dated Sep. 8, 2015 (now abandoned).
Final Office Action for U.S. Appl. No. 14/399,753, dated Mar. 30, 2016 (now abandoned).
Non-Final Office Action for U.S. Appl. No. 14/399,764, dated Dec. 17, 2015 (now abandoned).
International Search Report for counterpart Application No. PCT/EP2014/058896, dated Sep. 23, 2014.
International Search Report and Written Opinion for counterpart Application No. PCT/EP2014/058892, dated Oct. 29, 2014.
International Search Report for counterpart Application No. PCT/EP2014/058894, dated Sep. 29, 2014.
Oxford Dictionary, Half-Ester, http://www.oxfordreference.com/view/10.1093/acref/9780198529170.001.0001/acref-9780198529170-e-8589, retrieved online on Oct. 19, 2017 (Year:2017).
Final Office Action for U.S. Appl. No. 14/399,764, dated Aug. 5, 2016 (now abandoned).
Non-Final Office Action for copending U.S. Appl. No. 14/888,002, dated Sep. 9, 2016.
Non-Final Office Action for copending U.S. Appl. No. 14/787,983, dated Sep. 15, 2016.
Final Office Action for U.S. Appl. No. 14/399,753, dated Sep. 30, 2016 (now abandoned).
Non-Final Office Action for copending U.S. Appl. No. 14/888,013, dated Apr. 13, 2017.
Non-Final Office Action for U.S. Appl. No. 14/399,764, dated Mar. 8, 2017 (now abandoned).
Final Office Action for copending U.S. Appl. No. 14/787,983, dated May 30, 2017.
International Search Report for counterpart Application No. PCT/FR2015/051896, dated Oct. 19, 2015 (now abandoned).
International Search Report for counterpart Application No. PCT/EP2015/075061, dated Jan. 20, 2016.
International Search Report for counterpart Application No. PCT/EP2015/075062, dated Jan. 26, 2016.
MINTEL: "Code 10 Hair Styling Cream," XP007923186, Sep. 2001.
MINTEL: "One More Day Dry Shampoo," XP 007923187, Aug. 2013.
MINTEL: "Foot Deodorant Spray," XP007923193, Oct. 2013.
MINTEL: "72h Anti-Perspirant Deodorant," XP007923192, Jan. 2014.
MINTEL: "Dry Shampoo," XP007923191, Jan. 2014.
Non-Final Office Action for U.S. Appl. No. 15/324,804, dated Mar. 5, 2018 (now abandoned).
Non-Final Office Action for copending U.S. Appl. No. 15/523,232, dated Feb. 23, 2018.

(56) References Cited

OTHER PUBLICATIONS

Bezard et al., "Triglyceride Composition of Coconut Oil," Journal of American Oil Chemists' Society, 48, 3, Mar. 1971, pp. 134-139.
Non-Final Office Action for U.S. Appl. No. 15/523,242, dated Aug. 31, 2017 (now U.S. Pat. No. 10,449,140).
Final Office Action for copending U.S. Appl. No. 14/888,013, dated Aug. 15, 2017.
Final Office Action for copending U.S. Appl. No. 14/888,002, dated Sep. 21, 2017.
Final Office Action for U.S. Appl. No. 14/399,764, dated Aug. 16, 2017 (now abandoned).
Non-Final Office Action for U.S. Appl. No. 14/399,753, dated Oct. 4, 2017 (now abandoned).
Non-Final Office Action for copending U.S. Appl. No. 14/787,983, dated May 11, 2018.
Non-Final Office Action for U.S. Appl. No. 15/523,242, dated Mar. 27, 2018 (now abandoned).
International Search Report for counterpart Application No. PCT/EP2011/072617, dated Jul. 5, 2012 (now abandoned).
Todd, Charles, et al., "Volatile Silicone Fluids for Cosmetic Formulations," Cosmetics and Toiletries, vol. 91, Jan. 1976, pp. 29-32.
International Search Report for counterpart Application No. PCT/EP2016/050295, dated Mar. 23, 2016 (now U.S. Pat. No. 10,532,880).
International Search Report for counterpart Application No. PCT/EP2016/050299, dated Mar. 23, 2016.
International Search Report for counterpart Application No. PCT/EP2016/0503300, dated Mar. 16, 2016 (now U.S. Pat. No. 10,710,791).
Non-Final Office Action for U.S. Appl. No. 15/541,738, dated May 17, 2018 (now U.S. Pat. No. 10,532,880).
Non-Final Office Action for U.S. Appl. No. 13/993,413, dated May 19, 2015 (now abandoned).
Final Office Action for U.S. Appl. No. 13/993,413, dated Dec. 30, 2015 (now abandoned).
Non-Final Office Action for U.S. Appl. No. 13/993,413, dated Nov. 8, 2017 (now abandoned).
Final Office Action for U.S. Appl. No. 13/993,413, dated Jul. 5, 2018 (now abandoned).
Oxford Dictionary of Biochemistry and Molecular Biology (2 ed.), Half-Ester, http://www.oxfordreference.com/view/10.1093/acref/9780198529170.001.0001/acref-9780198529170-e-8589, retrieved online on Oct. 19, 2017 (Year:2017).
Final Office Action for U.S. Appl. No. 15/324,804, dated Nov. 30, 2018 (now abandoned).
Non-Final Office Action for U.S. Appl. No. 14/399,764, dated Dec. 5, 2018 (now abandoned).
Non-Final Office Action for U.S. Appl. No. 15/523,242, dated Dec. 17, 2018 (now U.S. Pat. No. 10,449,140).
Final Office Action for copending U.S. Appl. No. 14/787,983, dated Dec. 27, 2018.
Final Office Action for copending U.S. Appl. No. 15/523,232, dated Jan. 25, 2019.
Non-Final Office Action for U.S. Appl. No. 15/541,738, dated Feb. 5, 2019 (now U.S. Pat. No. 10,532,880).
Non-Final Office Action for copending U.S. Appl. No. 15/541,741, dated Feb. 27, 2019.
International Search Report for counterpart Application No. PCT/EP2015/064780, dated Sep. 14, 2015.
Porter, M.R., "Handbook of Surfactants," published by Blackie & Son (Glasgow and London), 1991, pp. 116-178.
MINTEL: "Styling Mousse," Nov. 2008, XP002736036.
Non-Final Office Action for copending U.S. Appl. No. 14/888,013, dated Mar. 14, 2019.
Mintel: "Clean Freak Refreshing Dry Shampoo," XP007923188, Demert Brands, Mar. 2014.
Final Office Action for U.S. Appl. No. 14/399,764, dated Jun. 7, 2019 (now abandoned).
Notice of Allowance for U.S. Appl. No. 15/523,242, dated Jun. 12, 2019 (now U.S. Pat. No. 10,449,140).
Non-Final Office Action for copending U.S. Appl. No. 14/787,983, dated Jun. 26, 2019.
Final Office Action for copending U.S. Appl. No. 15/541,741, dated Jul. 11, 2019.
Notice of Allowance for U.S. Appl. No. 15/541,738, dated Sep. 4, 2019 (now U.S. Pat. No. 10,532,880).
Supplemental Notice of Allowance for U.S. Appl. No. 15/523,242, dated Sep. 5, 2019 (now U.S. Pat. No. 10,449,140).
Non-Final Office Action for copending Application No. 15/322,771, dated Sep. 6, 2019.
Non-Final Office Action for U.S. Appl. No. 15/324,804, dated Oct. 10, 2019 (now abandoned).
Final Office Action for copending U.S. Appl. No. 14/888,013, dated Oct. 18, 2019.
Non-Final Office Action for copending U.S. Appl. No. 14/888,002, dated Oct. 7, 2019.
Non-Final Office Action for U.S. Appl. No. 15/541,743, dated Nov. 21, 2019 (now U.S. Pat. No. 10,710,791).
Non-Final Office Action for copending U.S. Appl. No. 15/523,232, dated Feb. 20, 2020.
Final Office Action for copending U.S. Appl. No. 14/787,983, dated Feb. 26, 2020.
Non-Final Office Action for copending U.S. Appl. No. 15/541,741, dated Mar. 3, 2020.
Clearco, "Cyclo-1400-DM D5 Cyclomethicone/dimethicone blend," ([retrieved from on-line website: http://www.clearcoproducts.com/cyclo-1400-d5-blend.html], 2013, pp. 1-2.
Wayback Machine to support publication year of Clearco (Year: 2013).
Notice of Allowance for U.S. Appl. No. 15/541,743, dated Mar. 18, 2020 (now U.S. Pat. No. 10,710,791).
Non-Final Office Action for copending U.S. Appl. No. 15/322,771, dated Mar. 20, 2020.
Final Office Action for U.S. Appl. No. 15/324,804, dated Apr. 20, 2020 (now abandoned).
Final Office Action for copending U.S. Appl. No. 14/888,002, dated Jun. 1, 2020.
Final Office Action for copending U.S. Appl. No. 15/322,771, dated Jul. 10, 2020.
Non-Final Office Action for copending U.S. Appl. No. 14/787,983, dated Jul. 15, 2020.
Final Office Action of copending U.S. Appl. No. 15/541,741, dated Sep. 17, 2020.
Final Office Action for copending U.S. Appl. No. 15/523,232, dated Oct. 1, 2020.
Final Office Action for copending U.S. Appl. No. 14/787,983, dated Feb. 19, 2021.
Non-Final Office Action for copending Application No. 15/322,771, dated Mar. 2, 2021.
Non-Final Office Action for copending U.S. Appl. No. 14/888,013, dated May 11, 2021.
Non-Final Office Action for copending U.S. Appl. No. 15/541,741, dated May 27, 2021.
Non-Final Office Action for copending U.S. Appl. No. 16/491,374, dated Jan. 14, 2021.
Non-Final Office Action for copending U.S. Appl. No. 16/491,375, dated Nov. 25, 2019.
Final Office Action for copending U.S. Appl. No. 16/491,375, dated May 26, 2020.
Final Office Action for copending U.S. Appl. No. 16/491,374, dated Jun. 28, 2021.
Non-Final Office Action for copending U.S. Appl. No. 14/888,002, dated Sep. 3, 2021.
Final Office Action for copending U.S. Appl. No. 14/888,013, dated Sep. 3, 2021.
Non-Final Office Action for copending U.S. Appl. No. 16/491,374, dated Oct. 20, 2021.

\* cited by examiner

AEROSOL DEVICE FOR DRY-WASHING AND TREATING THE HAIR

CROSS REFERENCE TO RELATED APPLICATIONS

This is a national stage application of PCT/EPEP2018/055882, filed internationally on Mar. 9, 2018, which claims priority to French Application No. 1751944, filed on Mar. 9, 2017, both of which are incorporated by reference herein in their entireties.

The present invention relates to a particular aerosol device comprising a cosmetic composition based on at least one powder, and to the use thereof for the dry-washing and cosmetic treatment of keratin materials, preferably human keratin fibres such as the hair.

In the field of washing keratin materials, dry shampoos have existed for many years, either in a powder form or in aerosol form. They enable excess sebum to be removed quickly and without wetting the head of hair. They act by taking up sebum by absorption by means of powders chosen for their sebum-absorbing qualities.

The powders used may be of mineral, organic, natural or synthetic origin and may be wheat, rice and corn starch derivatives.

In practice, the dry shampoos proposed are not entirely satisfactory, especially in terms of application and comfort. The aerosol sprays conventionally used generate a conical spray. This type of spray is not optimum for localized application, especially at the root, and it is generally uncomfortable to apply due to the quite large impact force on the head of hair.

Aerosol devices comprising three outlet orifices have already been proposed for dispensing dry shampoos, especially in patent application EP 2 991 612, the three orifices spraying the composition in the same direction.

Patent applications US 2002/0017575 and EP 2 444 160 describe spray devices comprising one or more spray stems pierced with orifices allowing a product to be diffused in the hair.

There is a need to further improve aerosol devices comprising a dry shampoo composition.

The Applicant has found, surprisingly and advantageously, that the use of a device equipped with a dispensing head comprising at least two outlet orifices for spraying the composition in at least two different directions and at least two chambers through which the composition stream successively passes before it exits via the outlet orifices, to dispense a composition comprising a powder, makes it possible to facilitate the application of the composition with better dispersion, by means of application in several preferred directions, and to offer greater comfort on application, especially at the root, while at the same time offering the cleansing properties expected of a dry shampoo.

The changes of direction of the composition stream in the dispensing head create turbulences in the composition stream, which produces good-quality sprays.

According to a first of its aspects, a subject of the invention is an aerosol device comprising:
- a container containing a cosmetic composition which comprises at least 7% by weight of one or more powders relative to the total weight of the composition, and
- a dispensing head comprising a body and an end part comprising at least two outlet orifices configured to allow spraying of the composition about a longitudinal axis of the end part in at least two different directions, the dispensing head comprising at least first and second chambers through which the composition stream successively passes before it exits via the outlet orifices.

This particular combination affords comfort on application by spraying directly under the head of hair.

It also makes it possible to facilitate the application by dispensing the hair composition optimally at the roots of the hair, and thus affords efficient cleansing.

Moreover, the composition leaves a lesser amount of white residues.

A styling effect may also be obtained, especially for the provision of volume and texturing to the head of hair and lifting of the roots.

The present invention also relates to a process for dry-washing and treating the hair, comprising the use of the device as defined previously. In particular, the process comprises a step of spraying of the composition according to the invention, using the aerosol device according to the invention, onto keratin materials.

Other subjects, characteristics, aspects and advantages of the invention will emerge even more clearly on reading the description and the example that follows.

In the text hereinbelow, and unless otherwise indicated, the limits of a range of values are included within that range, especially in the expressions "between" and "ranging from . . . to . . . ".

Moreover, the expression "at least one" used in the present description is equivalent to the expression "one or more".

According to the invention, the aerosol device comprises a container which contains a cosmetic composition comprising one or more powders.

The powder may be mineral or organic, preferably organic. It may especially be a filler; a pigment or a mixture thereof.

For the purposes of the present invention, the term "fillers" means natural or synthetic particles of any form, which are insoluble in the medium of the composition, irrespective of the temperature at which the composition is manufactured.

The fillers may be organic or inorganic, and may be of any form such as lamellar, spherical or oblong, irrespective of the crystallographic form (for example cubic, hexagonal, orthorhombic, rhombohedric or tetragonal). In a preferred embodiment, the fillers are not spherical.

For the purposes of the present invention, the term "pigments" means organic or mineral, white or coloured particles of any form, which are insoluble in the medium containing them and which give the composition a colour.

The term "mineral" encompasses natural or synthetic chemical compounds that are inorganic. Mineral substances are mainly in a crystalline form.

Examples of mineral or inorganic powders that may especially be mentioned include:
- fillers such as metal carbonates, oxides and sulfates such as those of alkaline-earth metals, aluminium, gallium and indium; silicates; modified or unmodified silicas; sericite, synthetic fluorophlogopite, talc; natural or synthetic mica, especially white mica, gold mica, red mica, black mica and mica-lithium oxide; calcium phosphate, silicic acid, silicic anhydride, silicon carbide, metal salts of tungstic acid, magnesium aluminate, bentonite, zeolites, smectite, hydroxyapatite, ceramic powder, boron nitride and glass or ceramic microcapsules;
- specific composite fillers such as those sold under the names Excel Mica, Excel Pearl and the powder La Vie by the company Miyoshi Kasei, Inc.;

white pigments such as titanium dioxide, zinc oxide, zirconium oxide and cerium oxide;

coloured pigments such as red iron oxide, yellow iron oxide, black iron oxide, chromium oxide, chromium hydroxide, Prussian blue, ultramarine blue, chromium hydrate, ferric blue, inorganic blue pigments, carbon black, lower titanium oxides, manganese violet, cobalt violet, and metal powders such as aluminium powder and copper powder;

nacreous pigments such as bismuth oxychloride, mica/titanium, essence of pearl, powder prepared by coating synthetic mica with titanium dioxide, powder prepared by coating silica flakes with titanium dioxide, which is available under the brand name Metashine from Nippon Sheet Glass Co., Ltd, powder prepared by coating alumina flakes with tin oxide and titanium dioxide, powder prepared by coating aluminium flakes with titanium dioxide, powder prepared by coating copper flakes with silica, sold by the company Eckert Inc, USA, powder prepared by coating bronze flakes with silica, and powder prepared by coating aluminium flakes with silica;

ultrafine powders, having a mean particle size of less than 0.1 µm, such as ultrafine titanium dioxide, ultrafine zinc oxide, ultrafine iron oxide, and ultrafine cerium oxide;

other powders such as the luminescent powder sold under the brand name Luminova Series by Mitsui & Co., Ltd., aluminium powder, stainless-steel powder, tourmaline powder, and amber powder; and a mixture thereof.

Examples of organic powders are starch powder or starch derivative powder, cork powder, quinoa powder, wool powder, polyimide powder (Nylon® or Orgasol® from Arkema), polyester powder, polyethylene powder, polypropylene powder, polystyrene powder, polyurethane powder, benzoguanamine powder, polymethyl benzoguanamine powder, tetrafluoroethylene powder, poly(methyl methacrylate) powder, cellulose powder, silk powder, silicone powder, silicone rubber powder, powders of synthetic resins such as a styrene/acrylate copolymer, a divinylbenzene/styrene copolymer, a vinyl resin, a urea resin, a phenolic resin, a fluoro resin, tetrafluoroethylene (Teflon®) polymers, a silicone resin, an acrylic resin, a melamine resin, an epoxy resin, and a polycarbonate resin, hollow polymer microspheres, such as those of poly(vinylidene chloride)/acrylonitrile, for example Expancel® (Nobel Industrie), or acrylic acid copolymers (Polytrap® from the company Dow Corning), silicone resin microbeads (for example Tospearls® from Toshiba), particles formed from polyorganosiloxane elastomers, microcrystalline fibre powder, starch powder, acylated lysine powder, poly-8-alanine, lauryllysine, powder of the metal salt of (long-chain alkyl)phosphate, metal soap powder, Colour Index (CI) yellow pigments, CI orange pigments and tar-based pigments prepared in lacquer form, and dyes existing in the natural state prepared in lacquer form.

The tar-based dyes include, for example, the dyes Red No. 3, Red No. 10, Red No. 106, Red No. 201, Red No, 202, Red No. 204, Red No. 205, Red No, 220, Red No. 226, Red No. 227, Red No. 228, Red No. 230, Red No. 401, Red No. 505, Yellow No. 4, Yellow No. 5, Yellow No. 202, Yellow No. 203, Yellow No. 204, Yellow No. 401, Blue No. 1, Blue No. 2, Blue No. 201, Blue No. 404, Green No. 3, Green No. 201, Green No. 204, Green No. 205, Orange No. 201, Orange No. 203, Orange No. 204, Orange No. 206, and Orange No. 207.

The natural dyes include powders such as carmine, laccaic acid, carsamine, brazilin and crocin.

The doped or undoped composite powder may also be suitable as base powder intended to undergo a surface treatment. Examples of the latter include the powder prepared by coating inorganic dye pigments such as red iron oxide with silicic anhydride, powders prepared by coating Nylon with white pigments and powders prepared by coating fillers with ultrafine white pigments.

The mineral powder(s) according to the invention may optionally be surface-modified with organic compounds.

In one variant of the invention, the powder is a mineral powder constituted of one or more water-insoluble mineral compounds.

For the purposes of the present invention, the term "water-insoluble" refers to a compound whose solubility at spontaneous pH in water at 25° C. and at atmospheric pressure is less than 0.1%.

The water-insoluble mineral compound(s) are preferably chosen from metal carbonates, oxides and sulfates, silicates, modified or unmodified silicas, mica, talc, and mixtures thereof.

Examples that may more particularly be mentioned include the carbonates, oxides and sulfates of alkaline-earth metals such as beryllium, magnesium, calcium, strontium, barium and radium, better still magnesium and calcium; the oxides, sulfates and carbonates of aluminium, gallium and indium; silicates such as kaolinite or kaolins (natural silicates containing kaolinite), silicates containing magnesium, particularly those containing an amount of magnesium of greater than 10% by weight (on a dry basis) expressed as magnesium oxide, such as Li—Mg—Na silicates, for instance Laponite XLG, provided by the company Rockwood; modified or unmodified silicas, better still modified silicas; mica; talc; and mixtures thereof.

Among the modified silicas, it is preferred to use surface-treated silicas such as hydrophobic silicas, for instance hydrophobic fumed silica of nanometric size and surface-treated with hexamethyldisilazane, such as the silica sold under the trade name Aerosil R812S or Aerosil R972 by the company Evonik, or HDK H115 by the company Wacker, or hydrophobic fumed silica surface-treated with dimethylsilane.

The powder may be a styling powder, i.e. it may have a capacity for shaping the head of hair or for ensuring the durability of this shaping.

The capacity for shaping or ensuring shaping durability of the powder may especially be due to its chemical nature and/or its geometrical form and/or its arrangement configuration during deposition onto the keratin fibre. Specifically, the irregularities created at the surface of the hair promote the inter-attachment of the fibres.

The powder may be of any form such as lamellar, spherical or oblong, irrespective of the crystallographic form (for example cubic, hexagonal, orthorhombic, rhombohedric or tetragonal). In a preferred embodiment, the powders are not spherical.

The number-average size of the powder may range from 0.001 to 50 µm, better still from 0.002 to 40 µm and even more preferentially from 0.003 to 35 µm.

This number-average size corresponds to the size measured from the statistical distribution of the particle sizes for half of the total number of the particles. This size is referred to as the D50.

In addition, the number-average size of these particles may be measured in the form of a mean value via an observation method with a light microscope, an electronic microscope, or a particle size analyser using laser scattering.

In the case where the particles are not in spherical form, their number-average size may be determined in the form of the mean of the longest or shortest diameter or of the thickness.

Preferably, the composition comprises at least one sebum-absorbing powder with a sebum uptake of greater than or equal to 35 ml/100 g.

For the purposes of the present invention, the term "sebum-absorbing powder" means a powder that is capable of absorbing and/or adsorbing sebum, which has a sebum uptake of greater than or equal to 35 ml/100 g.

The sebum uptake corresponds to the amount of sebum absorbed and/or adsorbed by the powder. It is expressed in ml of sebum per 100 g of powder and is measured using the method for determining the oil uptake of a powder described in standard NF T 30-022.

The oil uptake of a powder corresponds to the amount of sebum absorbed onto the available surface of the powder by measuring the "wet point" as indicated below.

The measuring method is as follows: an amount m (in grams) of between 0.5 and 5 grams of powder is placed on a glass plate, the amount depending on the density of the powder, followed by dropwise addition of artificial sebum having the following composition:

| | |
|---|---|
| triolein | 29% by weight |
| oleic acid | 28.5% by weight |
| oleyl oleate | 18.5% by weight |
| squalene | 14% by weight |
| cholesterol | 7% by weight |
| cholesteryl palmitate | 3% by weight |

After addition of 4 to 5 drops of artificial sebum, the artificial sebum is incorporated into the powder using a spatula, and the addition of the artificial sebum is continued until conglomerates of artificial sebum and of powder form. From this point, the artificial sebum is added at a rate of one drop at a time and the mixture is subsequently triturated with the spatula.

The addition of artificial sebum is stopped when a firm, smooth paste is obtained. This paste must be able to be spread over the glass plate without cracks or the formation of lumps. The volume Vs, in ml, of artificial sebum used is then noted.

The sebum uptake corresponds to the ratio Vs/m.

The sebum-absorbing powder(s) used in the aerosol device of the invention have a sebum uptake preferably ranging from 35 to 1000 ml/100 g and better still from 35 to 800 ml/100 g.

Advantageously, the sebum-absorbing particle may have a BET specific surface area of greater than or equal to 150 $m^2/g$, preferably greater than or equal to 300 $m^2/g$, better still greater than 500 $m^2/g$ and preferentially greater than 600 $m^2/g$, and especially less than 1500 $m^2/g$.

The BET specific surface area is determined according to the BET (Brunauer-Emmett-Teller) method described in the Journal of the American Chemical Society, vol. 60, page 309, February 1938, and corresponding to international standard ISO 5794/1 (appendix D). The BET specific surface area corresponds to the total specific surface area (thus including micropores) of the particle and especially of the powder.

The sebum-absorbing powder may be a mineral powder or an organic powder.

More specifically, the sebum-absorbing powder may be chosen from:
  starches,
  calcium silicates,
  perlites,
  zeolites,
  polylactic acids,
  silicas,
  polyamide (Nylon®) powders,
  powders of acrylic polymers, especially of polymethyl methacrylate, of poly(methyl methacrylate/ethylene glycol dimethacrylate), of poly(allyl methacrylate/ethylene glycol dimethacrylate), or of ethylene glycol dimethacrylate/lauryl methacrylate copolymer;
  powders of silicone elastomer, obtained especially by polymerization of organopolysiloxane containing at least two hydrogen atoms each bonded to a silicon atom and of an organopolysiloxane comprising at least two ethylenically unsaturated groups (especially two vinyl groups) in the presence of a platinum catalyst; and
  mixtures thereof.

The sebum-absorbing powder may be a powder coated with a hydrophobic treatment agent.

The hydrophobic treatment agent may be chosen from fatty acids, for instance stearic acid; metal soaps, for instance aluminium dimyristate, the aluminium salt of hydrogenated tallow glutamate; amino acids; N-acylamino acids or salts thereof; lecithin, isopropyl triisostearyl titanate, and mixtures thereof.

The N-acylamino acids may comprise an acyl group containing from 8 to 22 carbon atoms, for instance a 2-ethylhexanoyl, caproyl, lauroyl, myristoyl, palmitoyl, stearoyl or cocoyl group. The salts of these compounds may be the aluminium, magnesium, calcium, zirconium, zinc, sodium or potassium salts. The amino acid may be, for example, lysine, glutamic acid or alanine.

The term "alkyl" mentioned in the compounds cited previously especially denotes an alkyl group containing from 1 to 30 carbon atoms and preferably containing from 5 to 16 carbon atoms.

The starches that may be used in the present invention are, for example, corn starch, potato starch, tapioca starch, rice starch, wheat starch and cassava starch.

The starches may or may not be modified.

A modified starch is a starch that has been modified via processes known to those skilled in the art, for instance esterification, etherification, oxidation, acid hydrolysis, crosslinking or enzymatic conversion.

Non-limiting examples of modified starches include aluminium starch octenylsuccinate, sodium starch octenylsuccinate, calcium starch octenylsuccinate, distarch phosphate, hydroxyethyl starch phosphate, hydroxypropyl starch phosphate, sodium carboxymethyl starch and sodium starch glycolate.

In a particular embodiment, the starch is a starch octenylsuccinate, in particular of aluminium, the starch being corn, wheat or rice starch. Mention may be made especially of the product provided by AkzoNobel under the name Dry Flo Plus. Mention may also be made of rice starch, such as the product D.S.A.7 provided by the company Agrana Starch.

Preferably, the calcium silicates used as sebum-absorbing powder have a sebum uptake of greater than 200 ml/100 g, better still between 400 ml/100 g and 600 ml/100 g and more preferentially of about 475 ml/100 g.

The specific surface area (BET) preferably ranges from about 150 m$^2$/g to 600 m$^2$/g, better still from 300 m$^2$/g to 600 m$^2$/g and even more preferentially from 310 m$^2$/g to 350 m$^2$/g.

The size of the silicate particles is preferably less than 20 micrometres.

These calcium silicates are generally prepared by reaction of reactive silica with an alkaline-earth metal reagent, preferably an alkaline-earth metal oxide or hydroxide, and a source of aluminium such as sodium aluminate or alumina. As the final properties of the silicate depend on the reactivity of the silica, the preferred source of silica is the reaction product of a soluble silicate, such as sodium silicate, and of a mineral acid, such as sulfuric acid. Suitable amorphous synthetic alkaline-earth metal silicates are manufactured by the company J.M. Huber Corporation and are sold under the Hubersorb® names. Methods for preparing these silicas are disclosed in greater detail in U.S. Pat. No. 4,557,916. Other suitable silicates are available from J.M. Huber Corporation, such as the sodium aluminosilicate sold under the Zeolexg brand name and the sodium magnesium aluminosilicate sold under the Hydrex® brand name.

Sebum-absorbing powders that may also be used include perlites, which are generally aluminosilicates of volcanic origin and which have the following composition:

70.0%-75.0% by weight of silica SiO$_2$
12.0%-15.0% by weight of aluminium oxide Al$_2$O$_3$
3.0%-5.0% of sodium oxide Na$_2$O
3.0%-5.0% of potassium oxide K$_2$O
0.5%-2% of iron oxide Fe$_2$O$_3$
0.2%-0.7% of magnesium oxide MgO
0.5%-1.5% of calcium oxide CaO
0.05%-0.15% of titanium oxide TiO$_2$.

Examples of zeolites that may especially be mentioned include sodium or potassium aluminosilicate compounds such as the product provided by Zeochem under the name XMOL.

The polylactic acids that may be used in the present invention are in particular Accurel EP600 from AkzoNobel or the product provided under the name Lactic Acid Polymer 9105 by Dajac Labs.

Silica powders that may be mentioned include:
the porous silica microspheres sold under the name Silica Beads SB-700 by the company Miyoshi and the name Sunsphere® H51 or Sunsphere® H33 by the company Asahi Glass;
the polydimethylsiloxane-coated amorphous silica microspheres sold under the name SA Sunsphere® H33 or SA Sunsphere® H53 by the company Asahi Glass.

Mention may be made, as Nylon powder, of the Nylon powder sold under the name Orgasol® 4000 by the company Atochem.

Mention may be made, as acrylic polymer powder, of:
the polymethyl methacrylate powders sold under the name Covabead® LH85 by the company Wackherr;
the polymethyl methacrylate/ethylene glycol dimethacrylate powders sold under the name Dow Corning 5640 Microsponge® Skin Oil Adsorber by the company Dow Corning and the name Ganzpearl® GMP-0820 by the company Ganz Chemical;
the poly(allyl methacrylate/ethylene glycol dimethacrylate) powders sold under the name Poly-Pore® L200 or Poly-Pore® E200 by the company Amcol Health and Beauty Solutions Inc.; these powders have in particular a sebum uptake of greater than or equal to 1 ml/g, better still ranging from 1 ml/g to 20 ml/g;
the ethylene glycol dimethacrylate/lauryl methacrylate copolymer powders sold under the name Polytrap® 6603 from the company Dow Corning.

Mention may be made, as silicone elastomer powder, of the powders sold under the names Trefil® Powder E-505C and Trefil® Powder E-506C by the company Dow Corning.

Particularly preferably, the composition comprises at least one sebum-absorbing powder with a sebum uptake of greater than or equal to 35 ml/100 g.

Preferentially; the composition comprises at least one powder chosen from starches, calcium silicates, perlites, zeolites, polylactic acids, silicas, polyimide powders, acrylic polymer powders, silicone elastomer powders, and mixtures thereof.

Even more preferably, the composition comprises at least one powder chosen from modified starches such as starch octenylsuccinates and in particular aluminium starch octenylsuccinate; perlite, polylactic acids and zeolites, and better still from starch octenylsuccinates.

The composition may furthermore also comprise one or more powders comprising one or more water-insoluble mineral compounds chosen from metal carbonates; oxides and sulfates and silicates containing magnesium. Preferably, the water-insoluble mineral compound(s) are chosen from calcium carbonate, magnesium carbonate, alumina, barium sulfate and/or magnesium oxide, and better still calcium carbonate.

The powder(s) are preferably present in a total amount of greater than or equal to 7% by weight, better still in a total amount ranging from 7% to 30% by weight, better still from 8% to 25% by weight, even more preferentially from 8.5% to 20% by weight and better still from 9% to 15°/s by weight relative to the total weight of the composition.

The composition may also comprise one or more C2-C4 monoalcohols.

As C2-C4 monoalcohol(s) that may be used in the aerosol device of the invention, mention may be made especially of ethanol or isopropanol, or better still ethanol.

When they are present, the C2-C4 monoalcohol(s) are preferably present in an amount ranging from 1% to 70% by weight, better still from 5% to 60% by weight and even more preferentially from 10% to 50% by weight relative to the total weight of the composition.

The composition according to the invention may contain one or more additional organic solvents such as polyols, for instance glycerol, propylene glycol or polyethylene glycols.

It may also contain water.

Preferably, the composition according to the invention contains less than 5% by weight of water and preferably less than 3% of water relative to the total weight of the composition.

The container of the device according to the invention also comprises one or more propellants.

Examples of propellants that may be used in the aerosol device of the present invention are liquefied gases such as dimethyl ether, 1,1-difluoroethane, or C3-C5 alkanes, for instance propane, isopropane, n-butane, isobutane, pentane or isopentane, or compressed gases such as air, nitrogen or carbon dioxide, and mixtures thereof.

Mention may be made preferentially of C3-C5 alkanes and in particular propane, n-butane and isobutane, and mixtures thereof.

The propellant(s) may be present in the composition or, as a variant, in the container containing the composition, but separate from the composition.

The propellant(s) are preferably present in the composition.

When the propellant(s) are present in the composition, they are preferably present in an amount ranging from 10% to 95% by weight, better still from 15% to 90% by weight and even more preferentially from 20% to 88% by weight relative to the total weight of the composition.

The compositions defined in the invention may also contain one or more additives chosen from conditioning or fixing anionic, cationic, nonionic, amphoteric or zwitterionic polymers, fragrances, dyes, protective screening agents, acids, bases, nacres and glitter flakes.

These additives may be present in the composition according to the invention in an amount ranging from 0 to 20% by weight, relative to the total weight of the composition.

A person skilled in the art will take care to select these optional additives and the amounts thereof so that they do not harm the properties of the compositions of the present invention.

The compositions in accordance with the invention are packaged in an aerosol device comprising a container, also known as a reservoir.

The container is pressurized and comprises the composition to be dispensed. As already mentioned previously, the container contains both the propellant(s) and the other ingredients of the composition, in a single compartment, or as a variant in two compartments. According to the latter variant, the container may be constituted of an outer aerosol reservoir comprising an inner bag hermetically welded to a valve. The various ingredients of the composition are introduced into the inner bag and a propellant is introduced between the bag and the can at a sufficient pressure to make the composition come out in the form of a spray.

The propellant may be a compressed gas that is preferably used at a pressure of between 1 and 12 bar and better still between 9 and 11 bar.

The container is equipped at its top end with a valve that seals the system. The valves that are suitable for the devices according to the invention are especially valves with an internal restriction orifice of between 0.3 and 3 mm, preferably between 0.5 and 2.5 mm and even more preferentially between 0.6 and 1 mm. As a variant, it is possible for these valves to not comprise an internal restriction orifice. The valves may have a nozzle with at least one orifice, better still two orifices between 0.3 and 1 mm and preferably between 0.4 and 0.8 mm and even more preferentially between 0.5 and 0.7 mm in size. They may also be equipped with an additional gas intake (AGI).

They are in particular "powder" valves sold by the companies Precision, Coster, Seaquist and Lindal.

The device, packaged with such a valve, ensures the sealing of the system, and also the dispensing of the product from the container.

The aerosol device according to the invention also comprises a dispensing head comprising a body and an end part, especially a diffuser, which may be connected to the body. The end part comprises at least two outlet orifices configured to allow spraying of the composition about a longitudinal axis Y of the end part in at least two different directions, which may especially be diametrically opposite each other, the dispensing head comprising at least first and second chambers, through which the composition stream successively passes before it exits via the outlet orifices.

The first and second chambers may be concentric.

At least one aperture between the first and second concentric chambers may be angularly offset relative to at least one of the outlet orifices. This angular offset is to be understood as being an offset about the axis of the concentric chambers or about the axis of the device, for example.

Thus, the composition stream leaving the diffuser has in particular undergone at least two changes of direction of the stream in the diffuser, or even at least three changes of direction. The term "change of direction" should be understood as meaning that the composition stream passes from a first direction to a second direction, the two directions forming between themselves an angle preferably greater than 60°, or even greater than 90°, better still greater than 120°, or even greater than 150°. In one illustrative embodiment, the composition stream undergoes at least one change of direction of greater than 120°, or even greater than 150°, better still of the order of 180°.

When assembled, the body and the end piece may define several outlet orifices about a longitudinal axis Y of the end piece, in particular in at least two different directions, which are in particular diametrically opposite each other. Alternatively, the dispensing orifices may be formed directly in the diffuser. They may be formed in a curved portion of the diffuser, for example a portion with a hemispherical shape.

The use of the term "end part" does not exclude the possibility that the end piece may comprise an attached element defining the end of the dispensing head.

The concentric chambers may be at least partially annular or, indeed, annular. The dispensing head may in particular comprise a first inner chamber and a second outer chamber. The inner and outer chambers may be separated by a separation skirt. This skirt is able to ensure the leaktightness of the chambers.

This separation skirt may be pierced with at least one aperture, or at least two apertures, allowing the composition stream to pass through. Thus, the composition stream may be separated into at least two distinct streams. The apertures in the separation skirt may be distributed uniformly on the circumference of the separation skirt. For example, they may be diametrically opposite each other when there are two of them. There may be between 2 and 10 of them.

The second chamber may be surrounded by a peripheral skirt cooperating with the body in such a way as to ensure the closure of the second chamber.

The outlet orifices may be distributed uniformly on the circumference of the peripheral skirt. For example, they are diametrically opposite each other when there are two of them. There may be between 2 and 10 of them. They may be diametrically opposite each other in respective pairs.

The dispensing head may be configured to permit spraying of the composition through outlet orifices in at least one direction transverse to a longitudinal axis Y, in particular in at least two different directions, which are in particular diametrically opposite each other.

The outlet orifices may be coplanar and arranged in a plane inclined relative to the longitudinal axis X. The dispensing head may in particular comprise at least three coplanar outlet orifices, the directions of spraying being in particular arranged at at least 30°, or at least 60°, or at least 90° from each other.

The outlet orifices may be angularly offset relative to the aperture(s) of the separation skirt, each by an angle of between 0 and 180°, better still between 20 and 90°, better still between 30 and 80°, for example of the order of 45°.

The longitudinal axis Y of the diffuser may constitute an axis of symmetry of the diffuser.

The diffuser is preferably assembled with the body via the top of said body. The diffuser may define the upper axial end of the dispensing head.

The end part, in particular the diffuser, may comprise an upper face of generally curved shape with outward convexity.

The dispensing head may have a supply channel for the composition coming from the container. To this end, the body comprises a central channel intended to allow the composition stream to pass from the container to the diffuser.

The body may define a cannula through which said channel extends, this cannula having a longitudinal axis inclined relative to the longitudinal axis X of the container.

The central channel of the body may comprise a vertical portion, which extends in the longitudinal axis X of the device above the container, and an oblique portion, which is inclined by an angle γ relative to the vertical portion. The angle γ may be between 0 and 90°, better still between 5 and 40°, or between 10 and 30°, for example of the order of 15°. The oblique portion of the central channel can receive the diffuser.

The vertical portion of the central channel is intended to receive the stem of the dispensing valve of the container.

The device may be without a nozzle having swirl ducts, which fact simplifies its production. The dispensing orifices may preferably lead directly to the outside, without an attached nozzle. An attached nozzle is understood as a component having at least one outlet orifice and comprising a plane wall in which the outlet orifice is formed, and also a mounting skirt, which can be mounted on a centre post.

Each jet emerging from the diffuser may be oriented generally along an axis not parallel to a longitudinal axis X of the device, in particular obliquely, for example being inclined relative to the longitudinal axis of the device by an angle greater than 10°, better still greater than 20°, better still greater than 30°.

The flow emerging from each outlet orifice can be oriented perpendicularly relative to the axis Y of the diffuser, the outlet orifices being coplanar, for example, and having axes oriented perpendicularly relative to the axis Y of the diffuser.

Alternatively, the jet emerging from each outlet orifice can form an angle with the normal to this axis Y, in such a way that all the jets produce a resulting spray of substantially conical shape. This angle may be a non-zero angle, between 5 and 180°, better still between 10 and 90°, or between 20 and 80°, better still between 25 and 70°, for example of the order of 35°.

The device may comprise at least three outlet orifices, better still at least four outlet orifices, which are preferably not aligned. The distance between the farthest outlet orifices can be less than 25 mm, better still less than 20 mm, or less than 15 mm, for example of the order of 12 mm or 10 mm.

The dispensing of the composition can be triggered by tilting the body relative to the container.

A subject of the invention is also the use of the device as described above for spraying a composition through up to 360°.

The invention will be understood more clearly on reading the following detailed description of a non-limiting illustrative embodiment thereof and on examining the appended drawing, in which.

FIGS. 1 to 11 show a device 1 for spraying a composition, said device 1 comprising a container 2 containing the composition to be sprayed, and a dispensing head 3 which sits on top of the container 2. The initial pressure in the container is, for example, between 1 and 12 bar at 20° C.

The container 2 may comprise a valve holder cup (not shown) crimped onto a body of the container or formed in another way.

Figure 1:
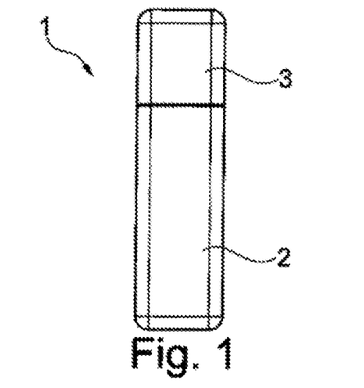
FIG. 1 is a side view of a spray device according to the invention.
Figure 2:
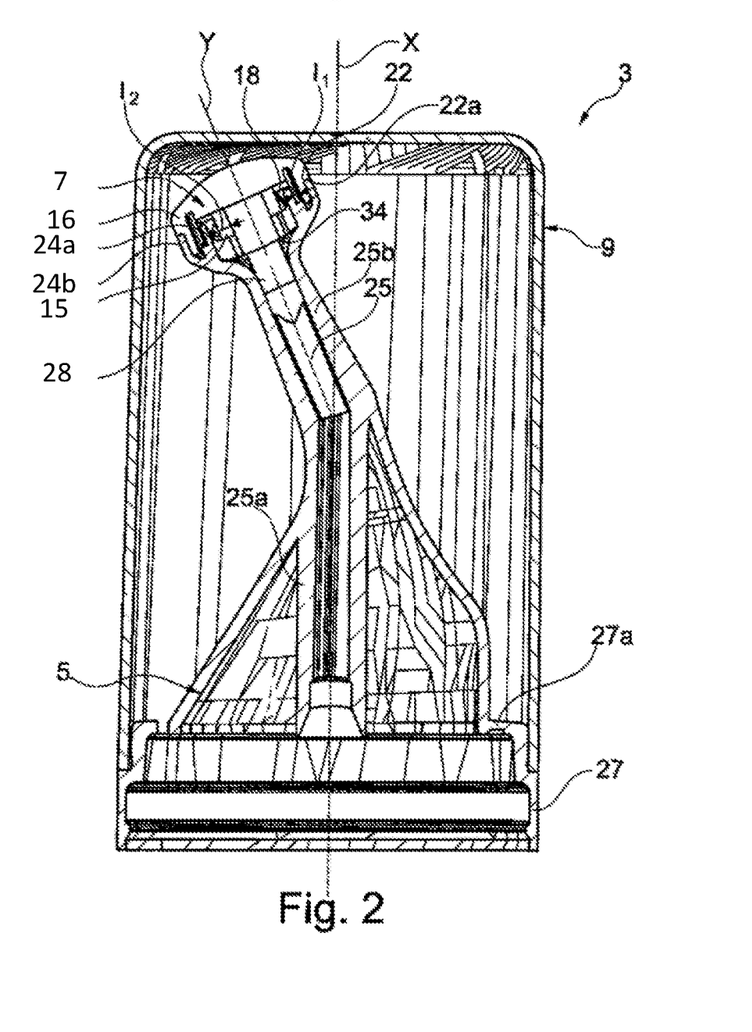
FIG. 2 is a longitudinal section through the dispensing head of the device in FIG. 1.
Figure 3:
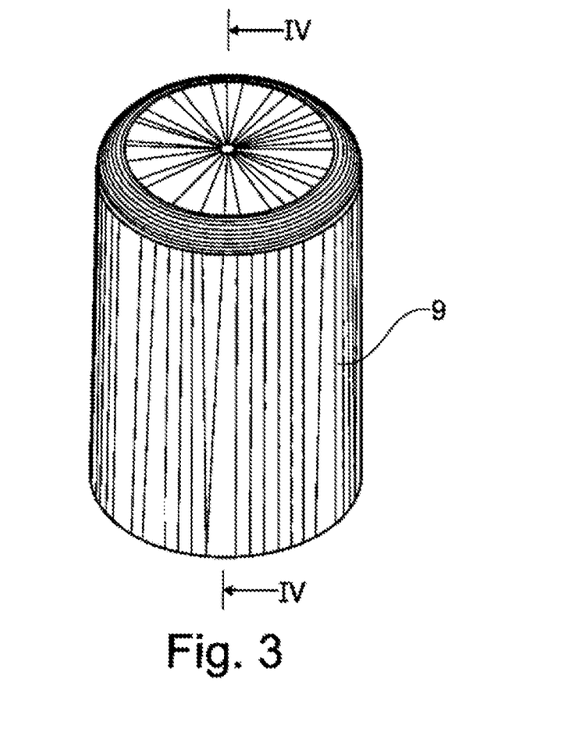
FIG. 3 is a perspective view of the closure cap of the device in FIGS. 1 and 2.
Figure 4:
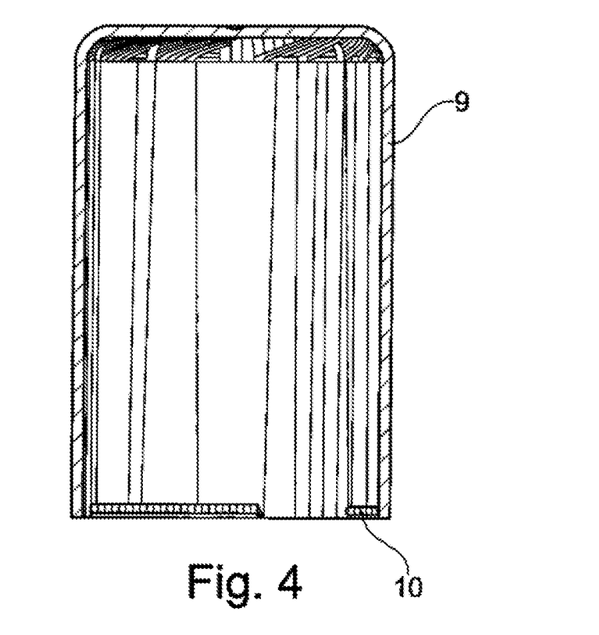
FIG. 4 is a longitudinal section of FIG. 3 along IV-IV.
Figures 5, 6, 7:
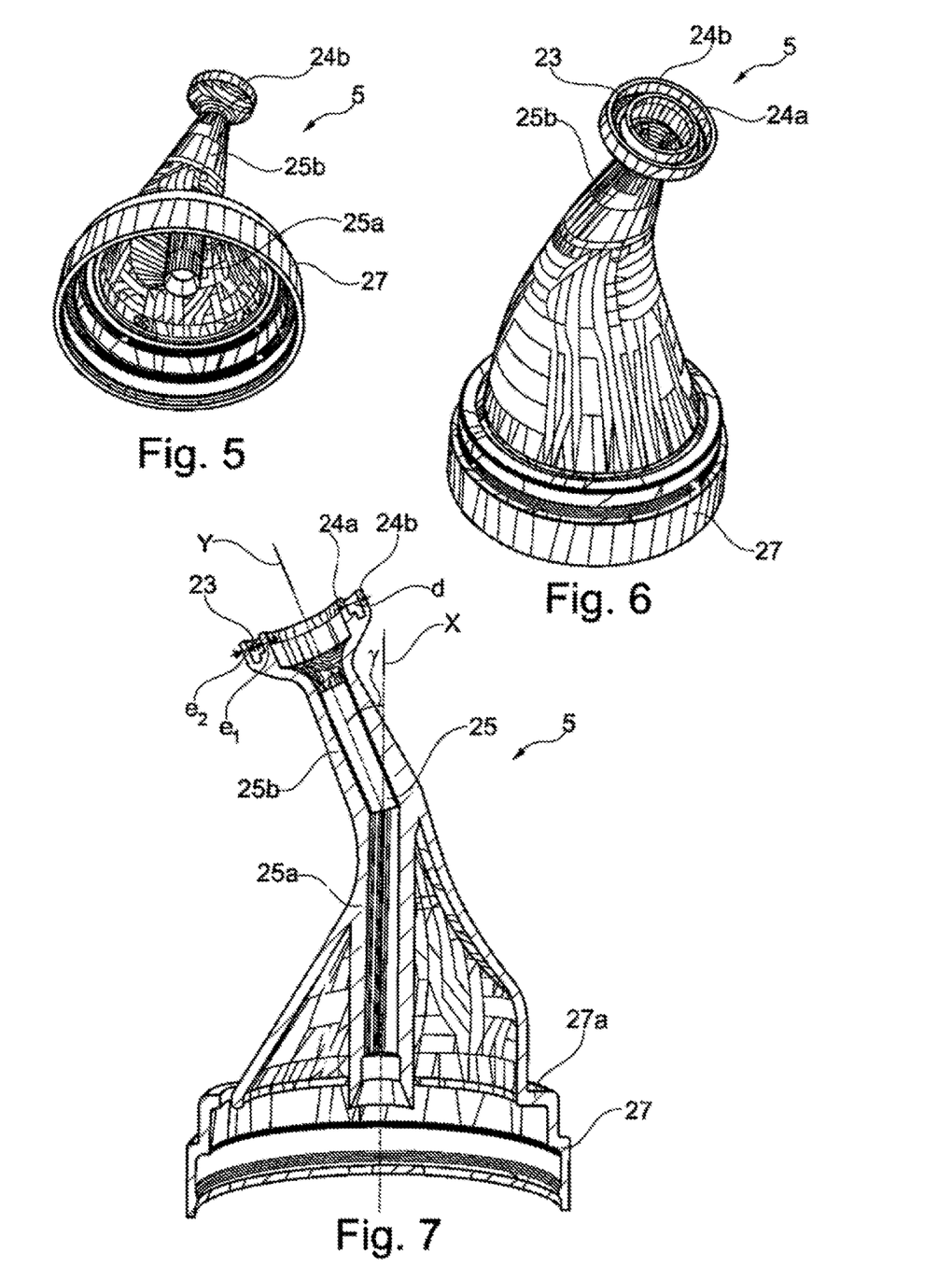
FIGS. 5 and 6 are perspective views of the body of the device in FIGS. 1 and 2.
FIG. 7 is a longitudinal section through the body in FIGS. 5 and 6.
Figure 8:
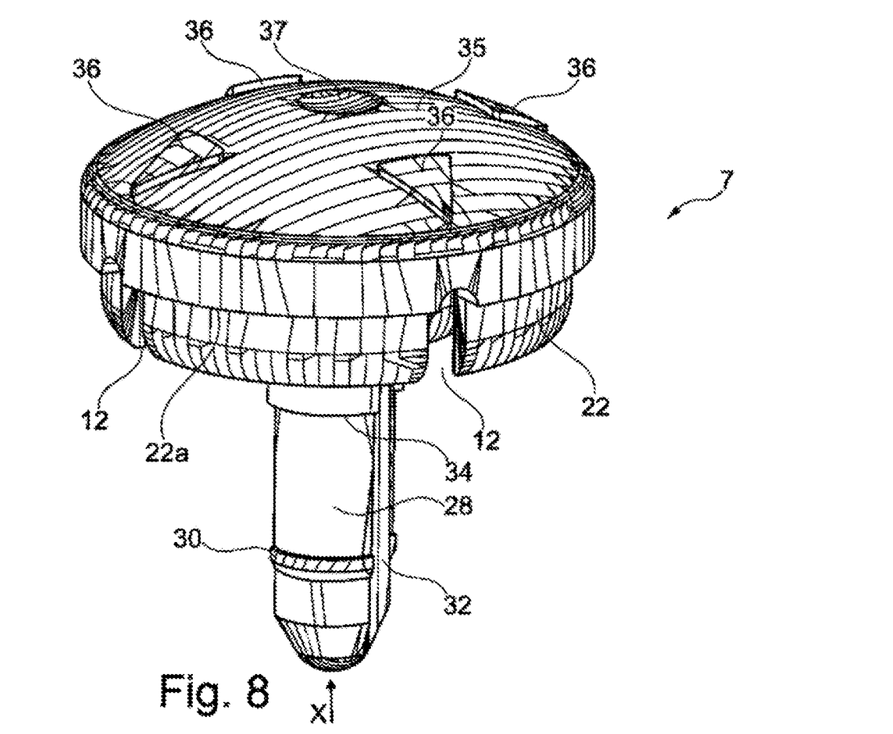
FIGS. 8 and 9 are schematic and partial perspective views of the diffuser in FIGS. 1 and 2.

The dispensing head 3 comprises a body 5 arranged on the container 2 and cooperating with a diffuser 7. A closure cap 9, visible in FIGS. 3 and 4, is intended to cover the body 5 and the diffuser 7 when the device is not in use. The cap 9 comprises, for example, an annular relief 10 in order to allow it to be held on the container 2 with snap-fit engagement.

The body 5 and the diffuser 7 are configured to allow the composition to be sprayed in at least two different directions, of which there are four in the example described, distributed uniformly about the axis Y of the diffuser. For this purpose, the diffuser 7 comprises four outlet orifices 12, visible in FIGS. 8 to 10, which will be described in detail below.

During the spraying of the composition, the composition stream coming from the container firstly passes through a central channel 25 of the body 5, which is intended to allow the composition to pass from the container 2 as far as the diffuser 7. This central channel 25 comprises a straight portion 25$a$, which extends in the longitudinal axis X of the device above the container, and an oblique portion 25$b$, which extends along the axis Y of the diffuser 7 and which is inclined by an angle γ relative to the straight portion 25$a$. The angle γ is of the order of 20 to 30', for example.

The diffuser 7 comprises a central stem 28 allowing it to be fixed to the body 5, in the oblique portion 25$b$. It is fixed by being inserted by force and with snap-fit engagement. For this purpose, the central stem 28 comprises a fixation relief 30, such as an annular bead, intended to snap-fit behind a corresponding relief of the body 5.

The central stem 28 has a shoulder 34 in order to guarantee leaktightness.

Two longitudinal grooves 32 formed on the central stem 28 allow the composition to pass from the body 5 towards the diffuser 7. They are diametrically opposite each other in the example described. These grooves 32 are oriented along the axis Y of the diffuser. They may have a cross section that is partially circular.

In the diffuser 7, the composition stream passes through a first inner chamber 15 and a second outer chamber 16 concentric to the first.

Figure 11:
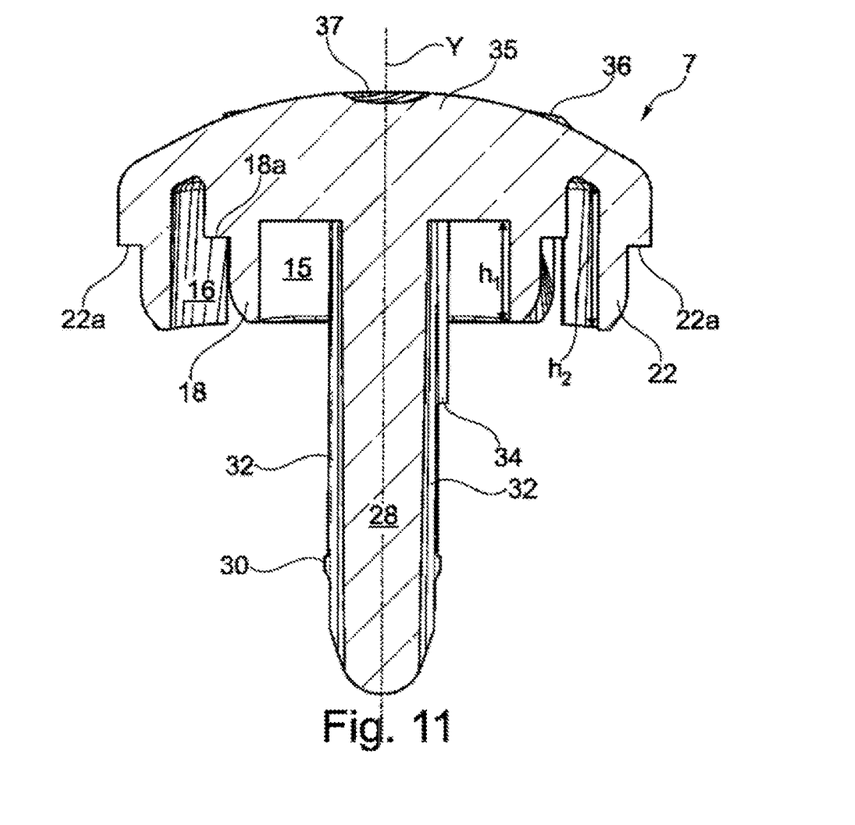
FIG. 11 is a longitudinal section along XI-XI in FIGS. 8 to 10.
Figure 12:
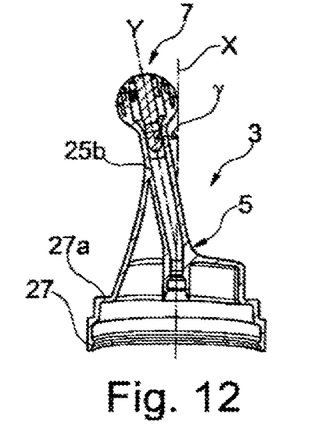
FIG. 12 is a view, similar to FIG. 7, of an alternative embodiment.
Figure 13:
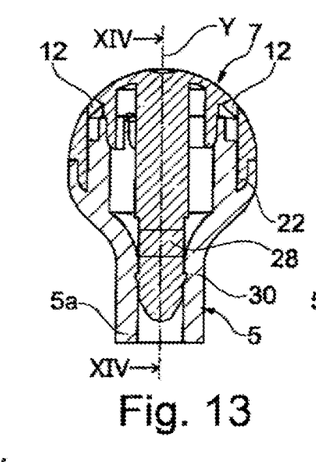
FIGS. 13 and 14 are partial longitudinal sections along XIII-XIII and XIV-XIV, respectively, in FIG. 12.
Figure 14:
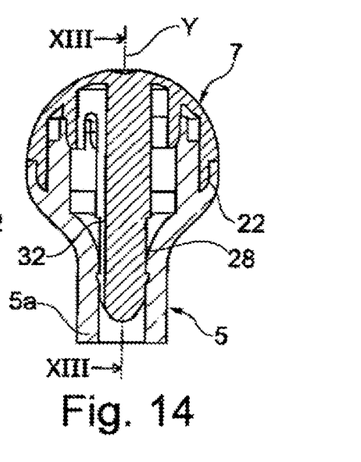
Figures 15, 16, 17:
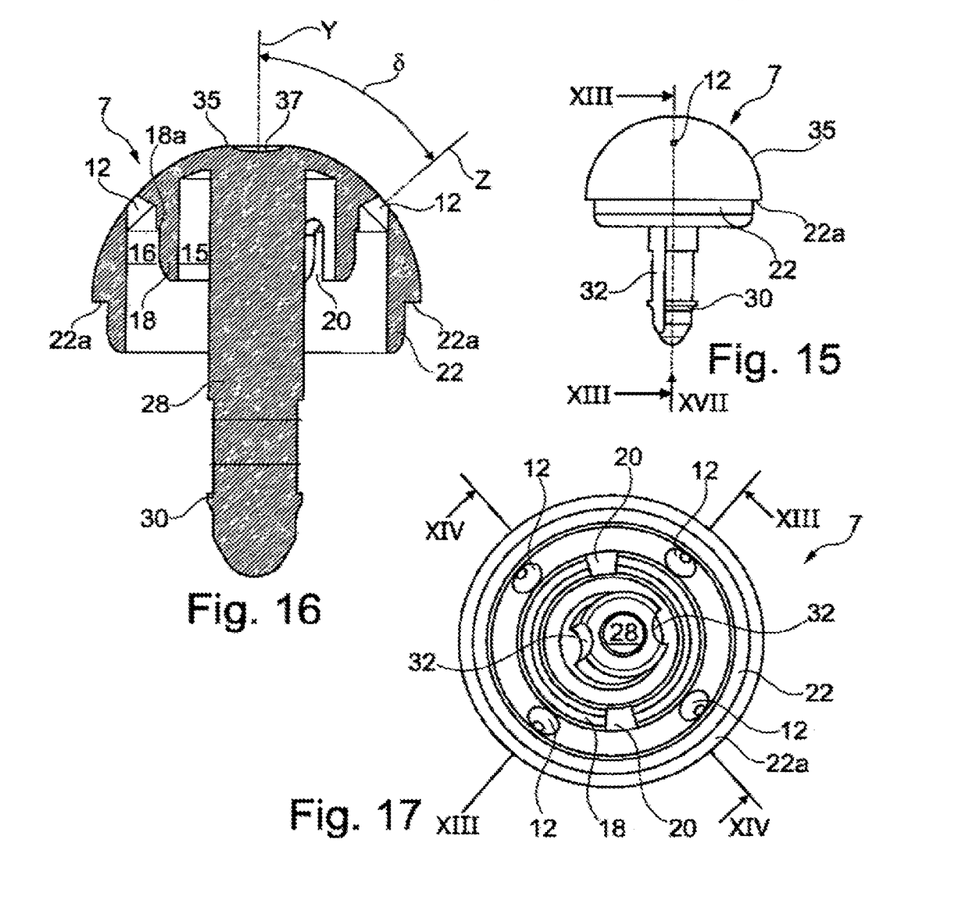
FIG. 15 is a perspective view of the diffuser in FIGS. 12 to 14.
FIG. 16 is a view, similar to FIG. 13, of the diffuser on its own.
FIG. 17 is a view of the diffuser in FIGS. 12 to 16 along the arrow XVII.
Figure 18:
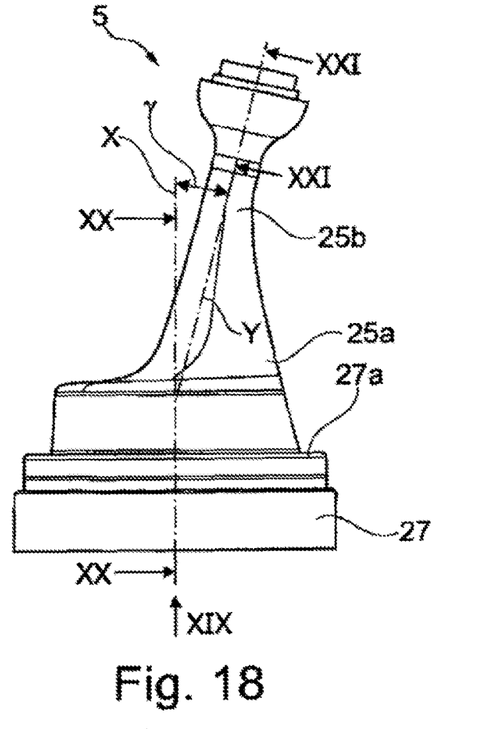
FIG. 18 is a side view of the body in FIGS. 12 to 17.
Figure 19:
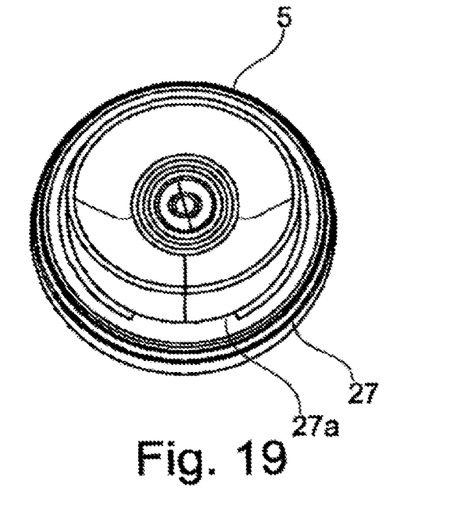
FIG. 19 is a view thereof along the arrow XIX.
Figure 20:
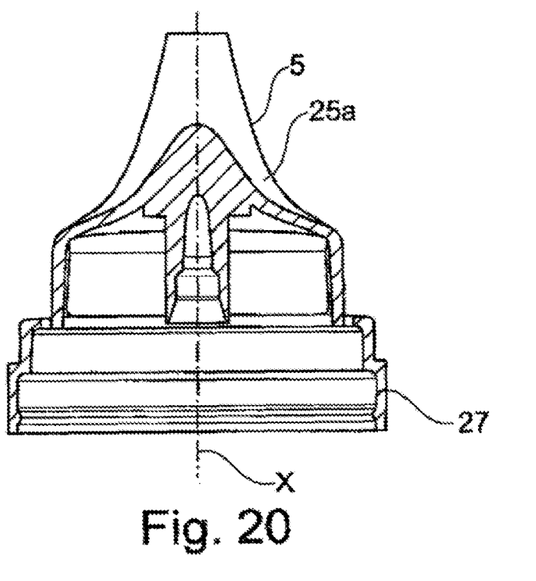
FIG. 20 is a cross-sectional view thereof along XX-XX.
Figure 21:
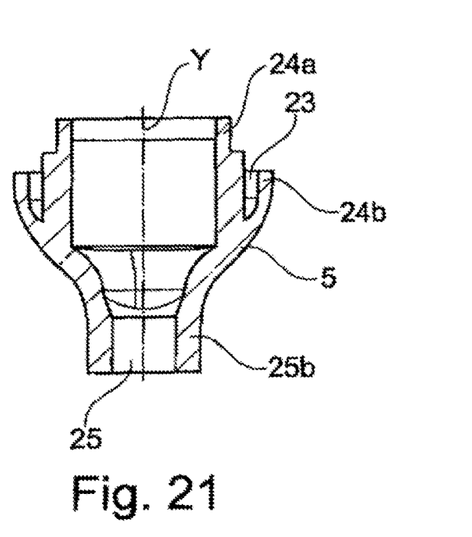
FIG. 21 is a cross-sectional view thereof along XXI-XXI.

The diffuser 7 comprises a separation skirt 18 between the first and second chambers 15 and 16. This separation skirt 18 is pierced with two apertures 20 to allow the composition stream to pass through. The latter is thus separated into four distinct streams, of which two opposite streams emerge from each of the apertures 20. The latter are uniformly distributed on the circumference of the separation skirt 18, being diametrically opposite each other. Each aperture 20 preferably extends along the entire height h1 of the separation skirt 18, as is illustrated in FIG. 11. The height h1 of the separation skirt 18 is of the order of 2.5 or 4 mm, for example.

The second chamber 16 is surrounded by a peripheral skirt 22 of the diffuser 7, said peripheral skirt 22 cooperating with the body 5 in such a way as to ensure the closure of the second chamber 16. The peripheral skirt 22 comprises the four abovementioned outlet orifices 12 for ensuring the discharge of the composition to the outside. These outlet orifices 12 are distributed uniformly about the axis Y of the diffuser 7, They may each extend along the entire height h2 of the peripheral skirt or along only part thereof. This height h2 may be of the order of 1.9 or 5 mm.

The chambers 15 and 16 preferably have respective widths 11 and 12 of the order of 1.2 mm.

The outlet orifices 12 may comprise a lower portion, in the form of a slit of constant width formed in the bottom of the skirt 22, and an upper portion, which has a semicircular cross section and is formed in the top of the skirt 22, extending away from the shoulder 22a. The composition emerges from the device via the upper portion of the outlet orifices 12, the lower portion being masked and closed by the body 5.

The outlet orifices may each have a cross section of between 0.05 and 5 $mm^2$, better still between 0.1 and 2 $mm^2$, for example of the order of 1 $mm^2$.

The outlet orifices may have any suitable geometric shape. In one embodiment, they may have a circular cross section.

Figure 10:
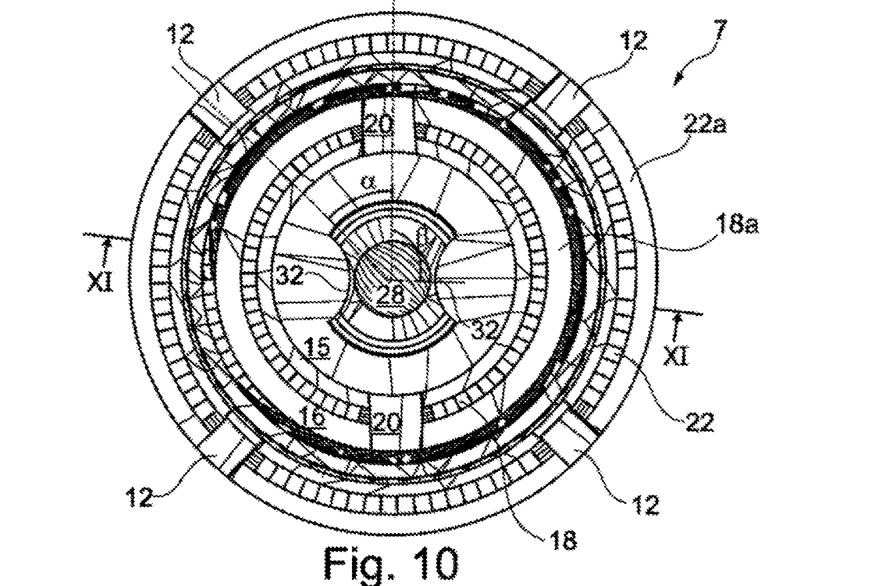
FIG. 10 is a bottom view along the arrow X in FIGS. 8 and 9.

The outlet orifices 12 are offset angularly relative to the apertures 20 of the separation skirt 18. For example, they are each offset by an angle α of the order of 45°, as illustrated in FIG. 10.

The apertures 20 are offset relative to the longitudinal grooves 32. For example, they are offset by an angle β of the order of 90°, as illustrated likewise in FIG. 10.

The body 5 comprises an annular groove 23 intended to receive the peripheral skirt 22 of the diffuser 7. This annular groove 23 is delimited by two concentric ribs 24a and 24b which are configured to engage on each side of the peripheral skirt 22. The two ribs 24a and 24b are continuous. They can bear against shoulders 22a and 18a, which are present on the separation skirt 18 and the peripheral skirt 22 respectively, when the body and the diffuser are assembled. They preferably have respective thicknesses e1 and e2 of the order of 0.7 mm. They form between them a distance d of the order of 1.25 mm. The rib 24b closes the lower portion of the outlet orifices 12.

The annular groove 23 and the ribs 24a and 24b are arranged at an end of the body opposite a mounting skirt 27 for mounting the body 5 on the container 2. The rest of the body, in particular the central channel 25 of the body, is connected to the mounting skirt 27 by a hinge 27a. The mounting skirt is preferably fixed with snap-fit engagement on the container, but it may also be fixed to the latter in another way.

The diffuser 7 has an upper face 35 with a generally curved shape, of which the radius of curvature is, for example, of the order of 6 mm.

The upper face 35 of the diffuser 7 has markers in the form of reliefs 36 with the general shape of a triangle, of which the point is oriented towards the edge of the upper face 35 and towards the peripheral skirt 22 alignment with the outlet orifices 12. The upper end 35 of the diffuser 7 likewise has a central depression 37, which has a circular contour and accommodates the injection sprue.

Figure 9:
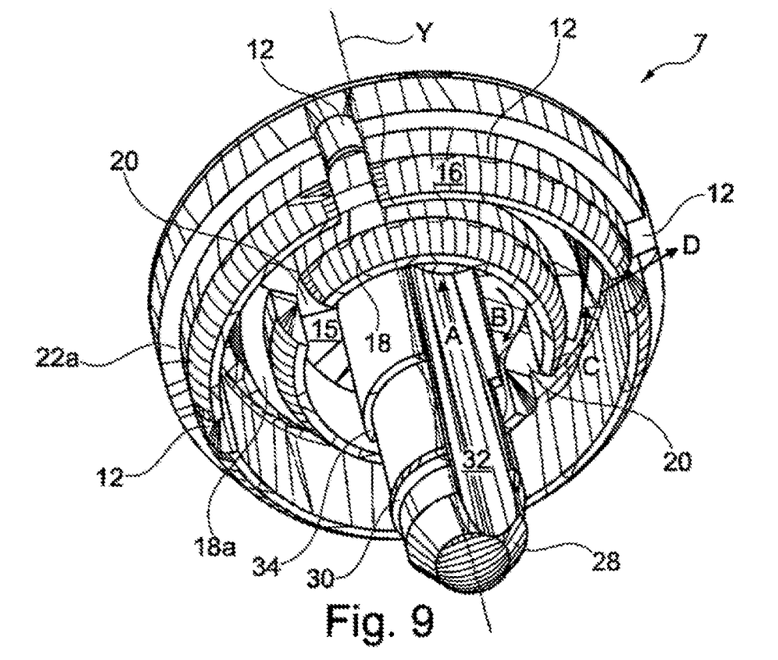

The composition stream undergoes at least two changes of direction in the diffuser 7. As illustrated in FIG. 9, the composition stream thus passes from a first direction A in the grooves 32 to a second direction B in the first chamber 15, the two directions A and B forming between them an angle of 90°. The composition stream then passes from the direction B to a direction C in the second chamber 16, with a change of direction of the order of 180°, then adopts a direction D corresponding to the emergence of the composition through an outlet orifice 12.

An alternative embodiment will now be described with reference to FIGS. 12 to 21. In this example, the outlet orifices 12 are formed in the diffuser 7 directly. They are formed in a curved portion of the diffuser 7, of hemispherical shape, having a radius of curvature of the order of approximately 6 mm.

The orifices 12 are each oriented outwards on an axis Z, which forms an angle with the axis Y of the diffuser. The angle δ is less than 90°, such that the resulting spray is of conical shape, with the composition being distributed all around the axis Y. The angle δ may be between 10 and 85°, better still between 20 and 80°, for example between 30 and 75°, or even between 40 and 70°. It can be of the order of 60°, for example.

The dispensing head in FIGS. 12 to 21 also differs from that of FIGS. 1 to 11 in terms of the shape of the body 5. In this illustrative embodiment, the latter comprises a cannula 25b through which said channel 25 extends, this cannula having a longitudinal axis Y inclined relative to the longitudinal axis X of the container.

In addition, the mounting skirt 27 for mounting the body 5 on the container 2 is connected to the rest of the body by a hinge 27a situated, relative to the longitudinal axis X, on the same side as the inclination of the axis Y, in such a way that the longitudinal axis Y of the cannula of a movable part of the body 5 is substantially parallel to the longitudinal axis X of the container during the dispensing of the composition.

The invention is not limited to the examples that have just been described.

For example, the valve of the container can be triggered by being pushed down and not by tilting.

The number of outlet orifices may be modified, as may their orientation.

The axes of the outlet orifices, along which axes the sprays are emitted, may or may not be coplanar, or they may or may not be contained in the same cone of axis Y.

The present invention also relates to a process for the dry-washing and cosmetic treatment of the hair, comprising the application to the hair, preferably dry hair, of a cosmetic composition as described above by means of an aerosol device as described above.

The application of the composition may optionally be followed by rinsing after an optional leave-on time, in the presence or absence of heat. Preferably, the application is not followed by rinsing.

The application of the composition may optionally be followed by brushing after an optional leave-on time, in the presence or absence of heat.

The present invention also relates to the use of the cosmetic composition defined above sprayed from the aerosol device according to the invention, for the dry-washing and cosmetic treatment of the hair.

The example that follows serves to illustrate the invention.

EXAMPLES

In the example that follows, all the amounts are indicated as weight percentages of product in unmodified form relative to the total weight of the composition.

The composition below was prepared from the compounds indicated in the table below.

|  | 1 |
|---|---|
| Aluminium starch octenylsuccinate[1] | 2% |
| Calcium carbonate (D50 = 35 µm)[2] | 5% |
| Hectorite modified with distearyldimethylammonium chloride[3] | 0.25% |
| Isopropyl myristate | 2% |
| Ethanol | 20.75 |
| Butane | qs 100% |

[1]Sold under the trade name Dry Flo Plus by National Starch (86% AM)
[2]Sold under the trade name Omyacare S60 by Omya
[3]Sold under the trade name Bentone 38 by Elementis In the example that follows, all the amounts are indicated as weight percentages of product in unmodified form relative to the total weight of the composition.

The composition below was prepared from the compounds indicated in the table below.

|  | A |
|---|---|
| Aluminium starch octenylsuccinate[1] | 10.92% |
| Calcium carbonate (D50 = 35 µm)[2] | 2.18% |
| Hectorite modified with distearyldimethylammonium chloride[3] | 0.28% |
| Isopropyl myristate | 0.20% |
| Zinc PCA (micronized zinc pyrrolidonecarboxylate) | 0.05% |
| Fragrance | 0.35% |
| Butane | qs 100% |

[1]Sold under the trade name Dry Flo Plus by National Starch (86% AM)
[2]Sold under the trade name Omyacare S60 by Omya
[3]Sold under the trade name Bentone 38 by Elementis The aerosol device D1 according to the invention, shown in FIGS. 12 to 21, was used to package the above compositions 1 and A. It comprises the following characteristics:

a valve equipped with a nozzle with an orifice 0.5 mm in size and an internal restriction orifice 0.8 mm in size, with an additional gas intake 0.40 mm in size, a dispensing head comprising a cannula which ends with a dome-shaped wall equipped with four outlet orifices of coplanar axes that are perpendicular to the longitudinal axis (Y) of the cannula, uniformly distributed about the axis Y, the four orifices being diametrically opposite each other in respective pairs. The outlet orifices have a cross section of 1 mm². The dispensing head comprises two concentric chambers communicating via two apertures offset by an angle α of the order of 45° relative to the outlet orifices.

An aerosol device D2 was moreover used to package composition A above. It comprises the following characteristics:

a valve equipped with a nozzle with an orifice 0.64 mm in size and an internal restriction orifice 0.64 mm in size, with an additional gas intake 0.64 mm in size, a dispensing head sold by the company Lindal under the name Tribuse and described in patent application EP 2991612, equipped with three orifices whose outlet axes are in the same direction, with a direct outlet 0.5 mm in diameter.

A standard aerosol device D3 was used to package the above composition A. It comprises the following characteristics:

a valve equipped with a nozzle with two orifices each 0.5 mm in size and an internal restriction orifice 0.8 mm in size, with an additional gas intake 0.4 mm in size, a dispensing head sold under the name Borsalino by the company Coster, equipped with a single outlet orifice with a direct outlet 0.5 mm in diameter.

Composition A was sprayed onto seven models having combination to greasy hair. The device D1 was used on one side of the head of hair, and the device D3 was used on the other side of the head of hair. In both cases, the same amount of composition was sprayed. The hair was then rubbed to spread the composition over the scalp, and then brushed per half-head.

After brushing, it is observed that the head of hair is visually less greasy after application of the composition with the device D1 according to the invention than after application of the same composition with the device D3. The hair also feels less greasy after application of the composition with the device D1 according to the invention than after application of the same composition with the device D3.

Composition A was also sprayed onto seven models having combination to greasy hair. The device D1 was used on one side of the head of hair, and the device D2 was used on the other side of the head of hair. In both cases, the same amount of composition was sprayed. The hair was then rubbed to spread the composition over the scalp, and then brushed per half-head.

After brushing, it is observed that the head of hair is visually less greasy after application of the composition with the device D1 according to the invention than after application of the same composition with the device D2. The hair also feels less greasy after application of the composition with the device D1 according to the invention than after application of the same composition with the device D2.

The invention claimed is:

1. An aerosol device comprising:
   a container containing a cosmetic composition which comprises from 7% to 30% by weight of a powder, relative to the total weight of the composition; and
   a dispensing head comprising:
   a body disposed on the container; and:
   a diffuser mounted to the body and comprising:
   a peripheral skirt comprising outlet orifices configured to spray the cosmetic composition in different directions with respect to a longitudinal axis of the diffuser;
   a separation skirt disposed within the peripheral skirt and comprising apertures;
   a central stem disposed within the separation skirt and comprising at least one longitudinal passage;

a first chamber formed between the central stem and the separation skirt; and a second chamber formed between the separation skirt and the peripheral skirt and concentrically surrounding the first chamber, wherein the diffuser is configured such that during dispensing, a portion of the cosmetic composition flows through the longitudinal passage in a first flow direction, flows through the first chamber in a flow second direction, flows through the second chamber in a third flow direction, and then flows through one of the outlet orifices in a fourth flow direction, with the first, second, third, and fourth flow directions being different from one another, and wherein the second and third flow directions are coaxial with respect to the longitudinal axis of the diffuser.

2. The aerosol device of claim 1, wherein the powder comprises a sebum-absorbing powder having a sebum uptake of greater than or equal to 35 ml/100 g.

3. The aerosol device of claim 2, wherein the sebum-absorbing powder is chosen from starch octenylsuccinates, calcium silicates, perlites, zeolites, polylactic acids, silicas, polyamide powders, acrylic polymer powders, silicone elastomer powders, or any combination thereof.

4. The aerosol device of claim 3, wherein the sebum-absorbing powder comprises an aluminum starch octenylsuccinate.

5. The aerosol device of claim 2, wherein the sebum-absorbing powder comprises one or more water-insoluble mineral compounds chosen from metal carbonates, metal oxides, metal sulfates, or magnesium silicates.

6. The aerosol device of claim 2, wherein the sebum-absorbing powder comprises calcium carbonate, magnesium carbonate, alumina, barium sulfate, magnesium oxide, or any combination thereof.

7. The aerosol device of claim 1, wherein:
a difference between the first flow direction and the second flow direction is about 90°; and
the second flow direction and the third flow direction are opposite coaxial directions.

8. The aerosol device of claim 1, wherein relative to the total weight of the cosmetic composition, the cosmetic composition comprises water in an amount of less than 5% by weight.

9. The aerosol device of claim 1, wherein the cosmetic composition comprises a propellant chosen from air, nitrogen, carbon dioxide, dimethyl ether, C3-C5 alkanes, 1,1-difluoroethane, or any combination thereof.

10. The aerosol device of claim 1, wherein the cosmetic composition comprises a propellant chosen from n-butane, propane, isobutane, or any combination thereof.

11. The aerosol device of claim 1, wherein relative to the total weight of the cosmetic composition the cosmetic composition comprises a propellant in an amount ranging from 10% to 95% by weight.

12. The aerosol device of claim 1, wherein axes of the outlet orifices are coplanar and extend perpendicular to the longitudinal axis of the diffuser.

13. The aerosol device of claim 1, wherein the diffuser comprises a dome-shaped wall comprising the outlet orifices.

14. The aerosol device of claim 1, wherein the body defines a cannula that extends along the longitudinal axis and is inclined relative to a longitudinal axis of the container.

15. The aerosol device of claim 1, wherein with respect to the longitudinal axis, the longitudinal passage is radially offset from the apertures, and the apertures are radially offset from the outlet orifices.

16. A method of dry-washing hair, the method comprising:
spraying the hair with an effective amount of a cosmetic composition;
wherein the cosmetic composition comprises from 7% to 30% by weight of a powder, relative to the total weight of the composition;
wherein the cosmetic composition is sprayed from a dispensing head comprising:
a body disposed on the container; and
a diffuser mounted to the body and comprising:
a peripheral skirt comprising outlet orifices configured to spray the cosmetic composition in different directions with respect to a longitudinal axis of the diffuser;
a separation skirt disposed within the peripheral skirt and comprising apertures;
a central stem disposed within the separation skirt and comprising at least one longitudinal passage;
a first chamber formed between the central stem and the separation skirt; and
a second chamber formed between the separation skirt and the peripheral skirt and concentrically surrounding the first chamber,
wherein the diffuser is configured such that during dispensing, a portion of the cosmetic composition flows through the longitudinal passage in a first flow direction, flows through the first chamber in a flow second direction, flows through the second chamber in a third flow direction, and then flows through one of the outlet orifices in a fourth flow direction, with the first, second, third, and fourth flow directions being different from one another, and
wherein the second and third flow directions are coaxial with respect to the longitudinal axis of the diffuser.

17. The method of claim 16, further comprising rinsing the cosmetic composition from the hair.

18. The method of claim 16, further comprising heating the cosmetic composition after spraying the cosmetic composition onto the hair.

19. The method of claim 16, wherein:
a difference between the first flow direction and the second flow direction is about 90°; and
the second flow direction and the third flow direction are opposite coaxial directions.

20. The method of claim 16, wherein with respect to the longitudinal axis, the longitudinal passage is radially offset from the apertures, and the apertures are radially offset from the outlet orifices.

* * * * *